US005693032A

United States Patent [19]
Bierman

[11] Patent Number: 5,693,032
[45] Date of Patent: Dec. 2, 1997

[54] CATHETER ANCHORING SYSTEM

[75] Inventor: Steven F. Bierman, Del Mar, Calif.

[73] Assignee: Venetec International, Inc., Mission Viejo, Calif.

[21] Appl. No.: 587,092

[22] Filed: Jan. 16, 1996

Related U.S. Application Data

[63] Continuation of Ser. No. 316,024, Sep. 30, 1994, abandoned.

[51] Int. Cl.$^6$ ............................................ A61M 5/32
[52] U.S. Cl. ................................... 604/180; 604/174
[58] Field of Search ............................... 604/174, 179, 604/180; 128/DIG. 26

[56] References Cited

U.S. PATENT DOCUMENTS

| | | |
|---|---|---|
| 2,707,953 | 5/1955 | Ryan . |
| 3,059,645 | 10/1962 | Hasbrouck et al. . |
| 3,064,648 | 11/1962 | Bujan . |
| 3,167,072 | 1/1965 | Stone et al. . |
| 3,482,569 | 12/1969 | Raffaelli . |
| 3,529,597 | 9/1970 | Fuzak . |
| 3,602,227 | 8/1971 | Andrew . |
| 3,677,250 | 7/1972 | Thomas . |
| 3,766,915 | 10/1973 | Rychlik . |
| 3,856,020 | 12/1974 | Kovac . |
| 3,900,026 | 8/1975 | Wagner . |
| 3,906,946 | 9/1975 | Nordstrom . |
| 3,973,565 | 8/1976 | Steer . |
| 4,020,835 | 5/1977 | Nordstrom et al. . |
| 4,059,105 | 11/1977 | Cutruzzula et al. . |
| 4,082,094 | 4/1978 | Dailey . |
| 4,129,128 | 12/1978 | McFarlane . |
| 4,161,177 | 7/1979 | Fuchs . |
| 4,224,937 | 9/1980 | Gordon . |
| 4,248,229 | 2/1981 | Miller .................................. 604/174 |
| 4,250,880 | 2/1981 | Gordon . |
| 4,316,461 | 2/1982 | Marais et al. . |
| 4,324,236 | 4/1982 | Gordon et al. . |
| 4,326,519 | 4/1982 | D'Alo et al. . |

(List continued on next page.)

FOREIGN PATENT DOCUMENTS

| | | |
|---|---|---|
| A20064284 | 4/1982 | European Pat. Off. . |
| 356683A | 7/1989 | European Pat. Off. . |
| 1184139 | 2/1959 | France . |
| 2381529 | of 1978 | France . |
| 2341297 | 8/1973 | Germany . |
| 2063679 | 11/1980 | United Kingdom . |
| WO80/01458 | 7/1980 | WIPO . |
| WO9219309 | 11/1992 | WIPO . |

OTHER PUBLICATIONS

Multiple–Lumen Central Venous Catheterization Product with ARROW+gard™ Antiseptic Surface (Arrow International brochure) (Apr. 1994).

Photographs (4) of Catheter Clamp and Rigid Fastener sold by Arrow International, Inc.

*Primary Examiner*—Sam Rimell
*Attorney, Agent, or Firm*—Knobbe, Martens, Olson & Bear, LLP

[57] ABSTRACT

An anchoring system for a central line catheter or other similar catheter or fluid lines provides convenient installation and release with a minimum of procedures and no pain or discomfort to the patient. The anchoring system includes a self-adhesive anchoring pad for secure mounting on the patient and an associated retainer. The retainer includes slotted openings to receive downwardly extending posts formed on the underside of lateral wings of a box clamp. The ends of the posts can be easily inserted into a large diameter central openings of the retainer holes and then slid horizontally to allow frictional or snap fit engagement and retention between the necks of the posts and the lateral slots or holes formed in the retainer. In this position, the ends of the posts are captured with a hollow within the retainer and beneath the lateral slots, and the box clamp and retainer thus are releasably locked together. The opposite sequence is followed for removal of the box clamp and catheter combination. A soft, pliable wing clamp also can be used in connection with the box clamp to retain the catheter and/or associated tubing within the box clamp.

38 Claims, 3 Drawing Sheets

U.S. PATENT DOCUMENTS

| | | |
|---|---|---|
| 4,362,156 | 12/1982 | Feller, Jr. et al. . |
| 4,397,647 | 8/1983 | Gordon . |
| 4,449,975 | 5/1984 | Perry . |
| 4,474,559 | 10/1984 | Steiger . |
| 4,480,639 | 11/1984 | Peterson et al. . |
| 4,633,863 | 1/1987 | Filips et al. . |
| 4,660,555 | 4/1987 | Payton . |
| 4,711,636 | 12/1987 | Bierman . |
| 4,742,824 | 5/1988 | Payton et al. . |
| 4,808,162 | 2/1989 | Oliver ................ 604/180 |
| 4,826,486 | 5/1989 | Palsrok et al. . |
| 4,852,844 | 8/1989 | Villaveces . |
| 4,857,058 | 8/1989 | Payton . |
| 4,863,432 | 9/1989 | Kvalo . |
| 4,898,587 | 2/1990 | Mera . |
| 4,919,654 | 4/1990 | Kalt . |
| 4,955,864 | 9/1990 | Hajduch . |
| 4,976,700 | 12/1990 | Tollini . |
| 4,997,421 | 3/1991 | Palsrok et al. . |
| 5,037,397 | 8/1991 | Kalt et al. . |
| 5,084,026 | 1/1992 | Shapiro . |
| 5,147,322 | 9/1992 | Bowen et al. . |
| 5,156,641 | 10/1992 | White . |
| 5,192,274 | 3/1993 | Bierman . |
| 5,322,514 | 6/1994 | Steube et al. . |
| 5,330,438 | 7/1994 | Gollobin et al. . |
| 5,338,308 | 8/1994 | Wilk . |
| 5,342,317 | 8/1994 | Claywell . |
| 5,344,406 | 9/1994 | Spooner . |
| 5,344,414 | 9/1994 | Lopez et al. . |
| 5,346,479 | 9/1994 | Schneider . |
| 5,352,211 | 10/1994 | Merskelly . |
| 5,354,282 | 10/1994 | Bierman . |
| 5,354,283 | 10/1994 | Bark et al. . |
| 5,380,293 | 1/1995 | Grant . |
| 5,380,294 | 1/1995 | Persson . |
| 5,380,301 | 1/1995 | Prichard et al. . |
| 5,382,239 | 1/1995 | Orr et al. . |
| 5,382,240 | 1/1995 | Lam . |
| 5,395,344 | 3/1995 | Beisang, III et al. . |
| 5,403,285 | 4/1995 | Roberts . |
| 5,413,562 | 5/1995 | Swauger . |
| 5,443,460 | 8/1995 | Miklusek . |
| 5,456,671 | 10/1995 | Bierman . |
| 5,468,228 | 11/1995 | Gebert . |
| 5,468,230 | 11/1995 | Corn . |
| 5,468,231 | 11/1995 | Newman et al. . |
| 5,470,321 | 11/1995 | Forster et al. . |
| 5,496,283 | 3/1996 | Alexander . |
| B1 5,147,322 | 1/1996 | Bowen et al. . |

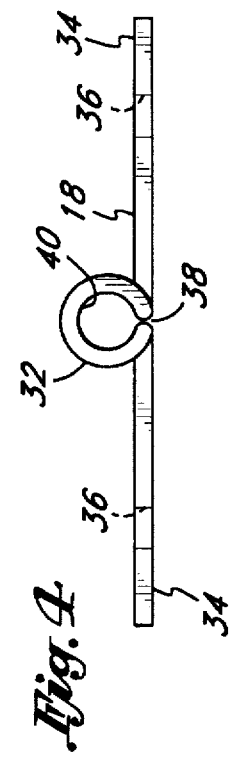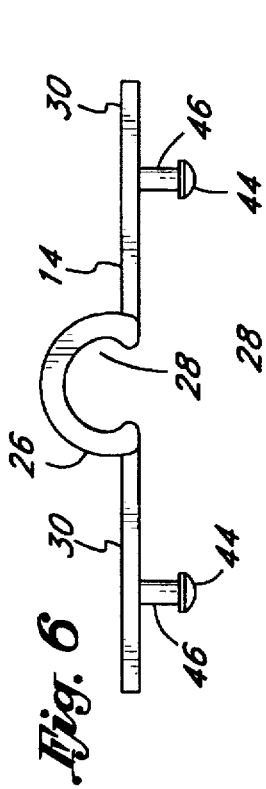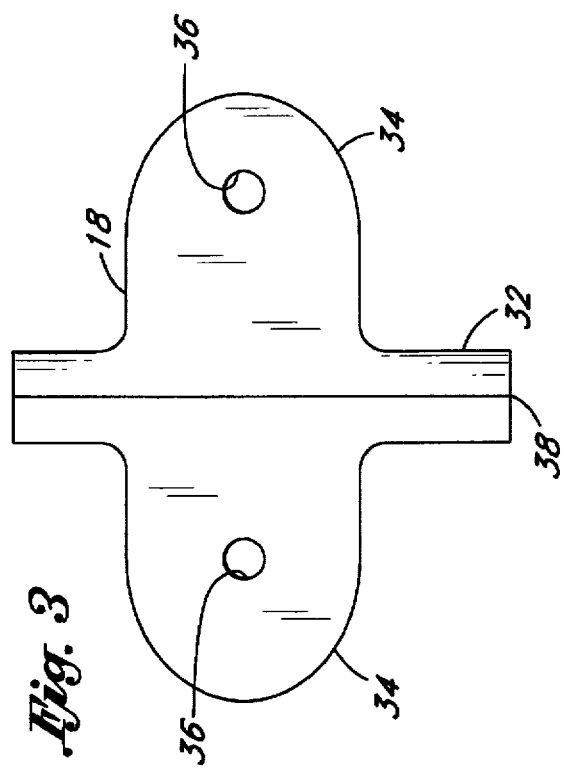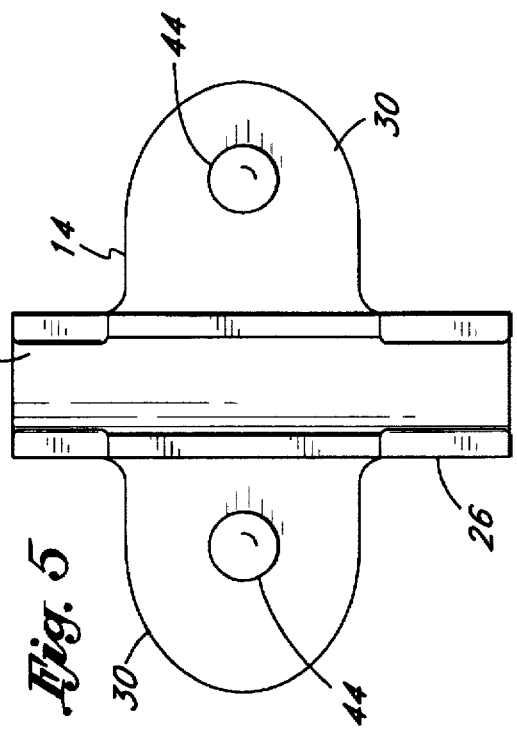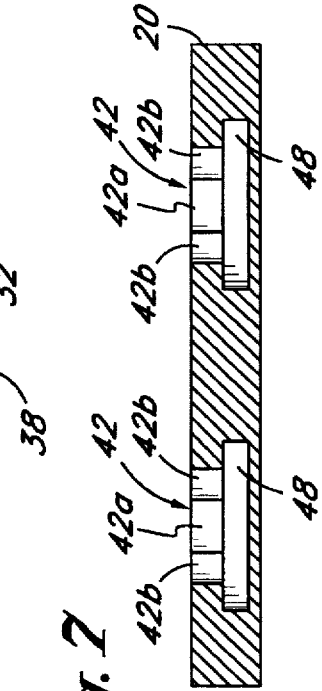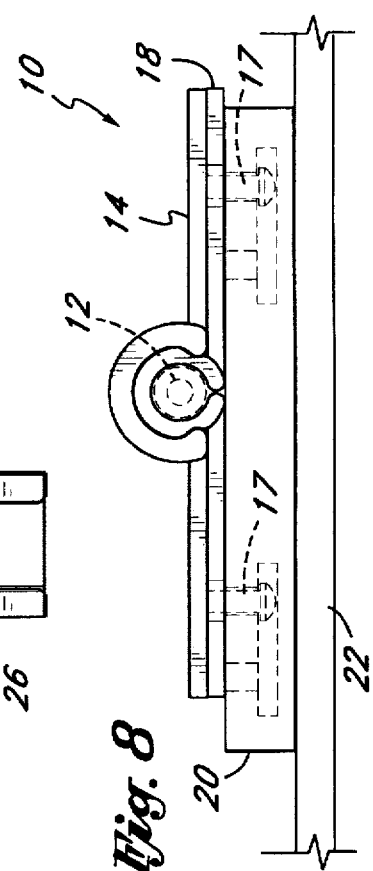

CATHETER ANCHORING SYSTEM

This application is a continuation of U.S. patent application Ser. No. 08/316,024, filed Sep. 30, 1994, now abandoned.

BACKGROUND OF THE INVENTION

1. Field of the Invention

The present invention relates to a catheterization system, and more particularly to an anchoring system for catheters and/or associated fluid supply or drainage lines.

2. Description of the Related Art

It is very common in the treatment of patients to utilize intravenous (IV) catheters to introduce fluids and medications directly into the bloodstream. In many cases, and particularly with respect to cardiac therapy, the IV catheter is introduced into a central venous line or a larger vein located close to the patient's heart. For example, a typical catheter utilized in connection with a central line is referred to as a "central venous catheter" ("CVC"), while a venous catheter peripherally inserted into the heart through a vein in the arm is sometimes referred to as a "peripherally inserted central catheter" ("PICC").

In these cases, long-term IV infusion typically requires that the catheter remain in place for many days. In order to secure such a central line IV catheter in position at the insertion site of the catheter, the IV tubing and/or CVC is commonly surrounded by a thin, winged, flexible pad or seat, which is then sutured to the patient's skin. In other applications, the thin, winged, flexible pad is covered by a more rigid clamp, which provides a friction fit for the catheter/pad combination. The rigid clamp and the flexible pad have lateral, aligned holes in them which allow the combination to be sutured to the patient's skin. Although this technique provides secure installation of the central line catheter, it obviously is painful and uncomfortable for the patient. This prior retention procedure also is time consuming and inconvenient, and poses the risk of needlestick to the nurse or other medical professional.

In U.S. Pat. No. 5,192,274 ("the '274 patent"), the present Applicant describes an anchoring system which provides for the convenient and pain-free installation of a central line catheter. Applicant hereby incorporates the '274 patent by reference. The anchoring system of the '274 patent includes an anchor pad which has an adhesive bottom surface that attaches to the patient's skin. Two posts on the pad slidable receive a conventional catheter seat or box clamp to secure the seat to the pad, but prevent disengagement of the seat from the pad. The posts are snipped or cut in order to remove the catheter.

SUMMARY OF THE INVENTION

In addition to incorporating the advantages of the anchoring system of the '274 patent, the anchoring system of the present invention also provides for releasible retention of the catheter and/or associated fluid line. That is, the present anchoring system releasible retains the catheter and/or fluid tubing to patient's skin in a manner which allows for convenient release and reattachment of the catheter or fluid line to the patient.

Thus, in accordance with one aspect of the present invention, an anchoring system for securing a catheterization device to the body of a patient is provided. The anchoring system includes a clamp which is configured to releasably engage a portion of the catheterization device. A retainer is connected to an adhesive layer for secure attachment to the body of the patient. The clamp and retainer including corresponding coupling structure which releasably engage to secure the clamp to the retainer.

In a preferred embodiment, the anchoring system is a multilevel system compatible with current venous catheter and retention systems. The anchoring system utilizes a soft split wing clamp, similar to one having present usage, as well as an overlying rigid box clamp. The box clamp engages the wing clamp from above and snaps on a portion of the central line catheter. However, unlike prior box clamps, the box clamp of the present invention includes one or more downwardly extending posts which are insertable into corresponding slotted holes within the retainer. The downwardly extending posts, in cooperation with the slotted holes of the retainer, provide an important advantage in connection with the convenient installation and easy release of central line catheters.

The retainer having the slotted holes is in turn secured on a self-adhesive foam anchor pad which can be easily and painlessly mounted on the skin of the patient by means of the self-adhesive backing. The retainer is mounted on this anchor pad by means of cyanoacrylate, or other bonding materials.

The slotted holes of the retainer correspond in number and location to the posts on the box clamp. Each post desirably includes a large diameter head or tip and a narrow neck or shank. The post tip is somewhat pointed or rounded in order to guide its insertion into the slotted holes, and the smaller diameter neck or shank mounts the tip to the underside of the box clamp. Each corresponding slotted hole in the retainer is formed by at least a larger diameter central hole and smaller diameter lateral, slot or hole. The diameter of the central hole is sufficient to receive the tip of the post, while the diameter of the lateral slots or holes provides a friction or snap fit with respect to the neck or shank of the posts. Thus, the retainer provides retention for the box clamp (and, in turn for the wing clamp and catheter), by freely receiving the end of each post, and then providing friction or snap fit engagement between the neck of the post and the lateral slots or holes. With the neck of the post positioned within the lateral slot or hole, the head of the post is captured within the retainer, beneath the slot, to releasably secure the box clamp to the retainer.

In use, the central line catheter is first inserted in accordance with standard procedure. The self-adhesive anchor pad is then adhered to the skin of the patient in such a manner so that its narrow neck region lies under the catheter and near the point of insertion. The soft split wing clamp is then placed over the shank of the catheter so that its longitudinal split is stretched and engages the catheter. The rigid box clamp is then snapped in place over the top of the wing clamp and the catheter shank in conventional fashion, such that a longitudinal groove formed in the box clamp engages the combination of the catheter and the wing clamp in a snap fit or friction fit engagement. The box clamp combination, including the wing clamp and catheter, is then aligned downwardly over the retainer such that the posts are aligned with the central slotted holes in the top surface thereof. These holes freely receive the posts as initial insertion occurs. Upon lateral movement of the box clamp, the neck of each post engages the lateral slots or holes of the retainer in a snap fit or friction fit engagement. This engagement then provides easy and convenient installation for the anchoring system.

During this installation process, the foam anchor pad serves to avoid any pain or discomfort to the patient by absorbing the downward force accompanying such installation. However, it should be noted that such force need only be very slight, as there is no resistance to initial insertion of the tip of the post into the central holes in the retainer. Firm force is required in only a lateral direction in order to secure the post to the lateral slots, such lateral movement being less painful for the patient.

In order to remove the catheter for replacement, cleaning, and the like, the opposite procedure is followed. The box clamp is simply moved laterally so that the neck of the post disengages the lateral hole or slot. The box clamp can then be easily lifted upward and removed from the retainer so that the tip of the post exits the central hole in the retainer.

Accordingly, the present invention provides secure anchoring, as well as convenient removal.

In accordance with another aspect of the present invention, an anchoring system is provided for securing a catheterization device to the body of a patient. The anchoring system includes an anchor pad having an adhesive layer for secure attachment to the body of the patient. A retainer is attached to the pad, and a clamp is configured to releasably engage a portion of the catheterization device. A coupling releasably interconnects the clamp to the retainer. The coupling includes at least one post and at least one slotted hole. The slotted hole receiving the post in a first position, and the post is movable from the first position to a second position within the hole. The coupling interconnects the retainer and clamp with the post in the second position.

In accordance with a preferred method of attaching a catheterization device to a body of a patient, a retainer, which is coupled to an adhesive member, is provided. The retainer is attached to the body by placing the adhesive member on the body. A clamp, which also is provided, is engaged with a portion of the catheterization device. The retainer and clamp are then coupled together in a releasable manner.

BRIEF DESCRIPTION OF THE DRAWINGS

These and other features of the invention will now be described with reference to the drawings of a preferred embodiment which is intended to illustrate and not to limit the invention, and in which:

FIG. 3 is a bottom plan view of a wing clamp utilized in connection with the present anchoring system;

FIG. 4 is an elevational end view of the wing clamp of FIG. 3;

FIG. 5 is a bottom plan view of the box clamp of the present anchoring system illustrating the longitudinal groove for receiving the central line catheter and the downwardly extending posts mounted on the lateral wings of the box clamp;

FIG. 6 is an elevational end view of the box clamp of FIG. 5 illustrating the lateral, downwardly extending mounting posts;

FIG. 7 is a cross-sectional view of the retainer or anchor base of the present anchoring system illustrating the slotted holes formed in the top surface of the retainer and the relief there below to receive the posts of the box clamp;

FIG. 8 is an elevational end view of the anchoring system of FIG. 1; and

DETAILED DESCRIPTION OF THE PREFERRED EMBODIMENTS

Figure 1:
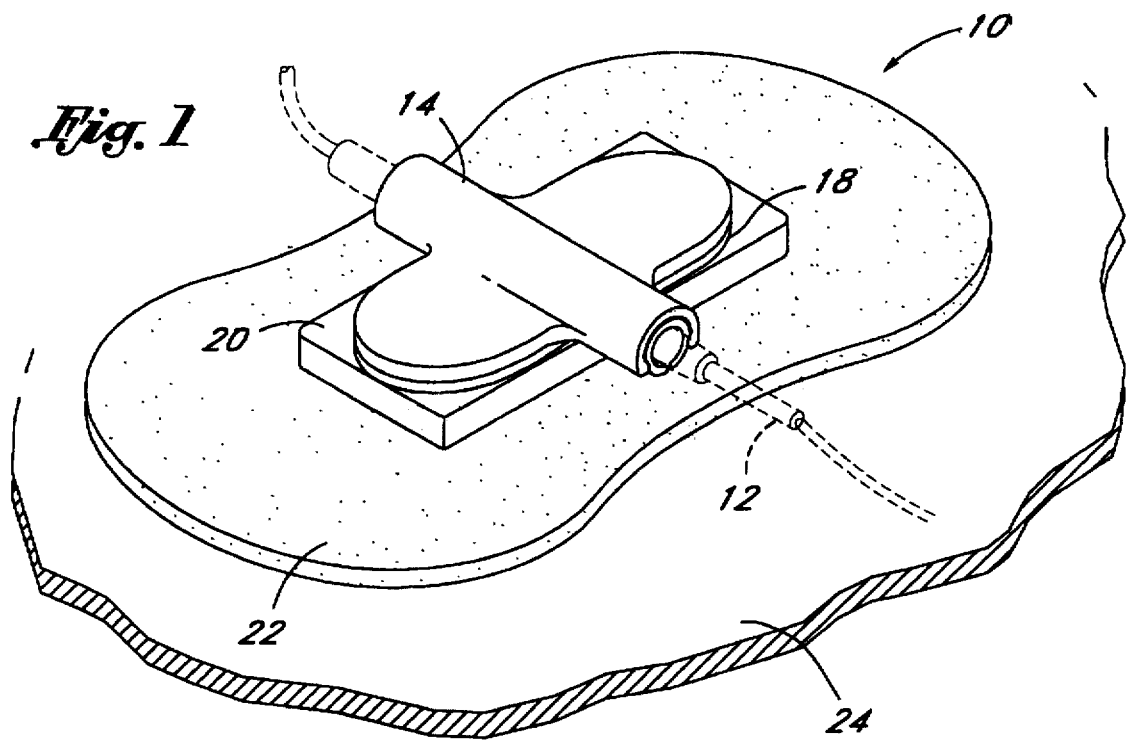
FIG. 1 is a perspective view of the central line catheter anchoring system of the present invention shown in use in connection with the central line catheter.

FIG. 1 illustrates an anchoring system 10 which is configured in accordance with a preferred embodiment of the present invention and is used in connection with a central line catheter 12. It is understood, however, that the anchoring system of the present invention also can be successfully utilized in connection with other types of catheters and catheterization devices utilized in a variety of different applications (e.g., arterial, intravenous, epidural, etc.), as well as with electrical wires or cables connected to external or implanted electronic devices or sensors. Thus, as used herein, the term "catheterization device" is meant generically to include catheters, fluid supply and drainage lines, connectors, adaptors, electrical wires and cables, and the like, all of which may be retained by the present anchoring system. It therefore should be understood that the principles of the present invention are not limited to central line catheters or peripherally inserted central catheters.

FIG. 1 illustrates the catheter 12 being anchored in position by an overlying box clamp 14 of the anchoring system 10. The box clamp 14 overlies and engages a soft wing clamp 18 which surrounds a portion of the catheter 12. The box clamp 14 and the wing clamp 18, which have similar configurations, engage an anchor base or retainer 20 which underlies the catheter 12. The retainer 20 in turn is mounted on an anchor pad 22 which is attached directly to the skin 24 of the patient by means of a self-adhesive backing (not shown). Thus, by means of cooperation between the box clamp 14 and the retainer 20, as described below in more detail, the catheter 12 may be conveniently and painlessly anchored to and released from the patient's skin.

Figure 2:
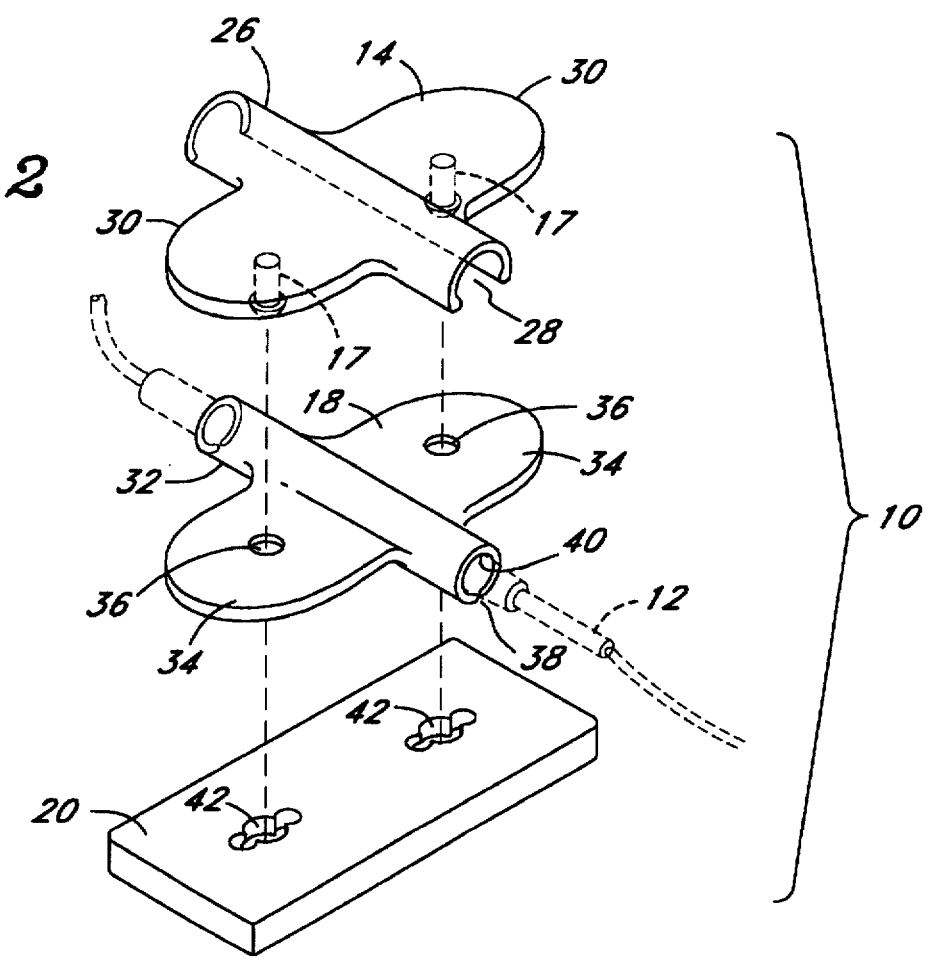
FIG. 2 is an exploded perspective view illustrating certain elements of the anchoring system of the present invention.

FIG. 2 illustrates the retainer 20 and clamp components of the present anchoring system 10. The box clamp 14, shown in the upper portion of FIG. 2, is a relatively small, wing-shaped device having a configuration similar to that of conventional box clamps in common usage today. The box clamp 14 includes a central elongate body 26 having a longitudinal groove 28 formed therein and a pair of lateral wings 30 extending transversely from the body 26. The longitudinal groove 28 (as best seen in FIGS. 2, 5 and 6) is generally U-shaped and is sized to receive the body of the catheter 12 and/or the associated fluid line, and more preferably is sized to receive the wing clamp 18 which surrounds a portion of the catheter 12 and/or the associated line. At at least one end, and preferably at both ends of the longitudinal groove 28, the body 26 of the box clamp 14 narrows the opening of the longitudinal groove 28. That is, the longitudinal groove 28 at either end extends through an arc, which is greater than 180 degrees about an axis of the longitudinal groove 28, so as to retain the wing clamp 18 within the body 26 of the box clamp 14. The groove 28 also can have a uniform cross section along its length so that the wall of the entire groove 28 extends through an arc greater than 180°.

The box clamp 14 is constructed of a substantially rigid plastic material, such as, for example, a polymer plastic material.

FIGS. 5 and 6 illustrate the box clamp 14 in greater detail, including the downwardly extending posts 17, shown best in FIG. 6. Each post comprises a tip or head 44 and a neck or shank 46 which connects the tip 44 to the underside of the lateral wings 30 of the box clamp 14. At least a portion of the tip 44 is larger than the diameter of the shank 46. In the illustrated embodiment, the tip 44 generally has a hemispherical shape; however, it is understood that other shapes, such as barbs, spheres, mushroom-shaped heads, and other types of radically projecting structures can be used as well. The tip 44 also is larger than the diameter of the lateral hole 42b. These posts 17 are aligned with the holes 36 in the wing clamp 18, although such posts can have other locations and configurations other than those shown and described herein to provide snap fit or friction fit engagement.

With reference to FIGS. 2–4, the wing clamp 18 has a configuration similar to that of the box clamp 14, including a central elongate body 32 and lateral wings 34 with holes 36 passing therethrough. The wing clamp 18 is constructed from a soft, pliable or flexible material such as, for example, Latex or the like. The body 32 generally has a tubular shape with an inner lumen 40 sized to surround a portion of the catheter body 12. The central elongate body 32 includes a slit 38 along its underside which can be expanded due to the pliable nature of the wing clamp 18. Thus, the wing clamp 18 is capable of surrounding and engaging longitudinally a portion of the catheter 12 to provide a secure means for engaging and retaining the catheter 12 in place.

FIGS. 3 and 4 illustrate in greater detail the split or grooved wing clamp 18 used in connection with the present invention. The central elongate body 32 is shown with a groove or split 38 formed longitudinally therein to provide a central longitudinal opening 40 to receive a portion of the catheter 12. The lateral wings 34 of the wing clamp 18, due to its soft, flexible construction, can be manually stretched in opposite directions to enlarge the width of the central split or groove 38 in the wing clamp, thereby providing a large enough central longitudinal opening 40 to engage a portion of the catheter 12.

As seen in FIGS. 1 and 8, the combination of catheter 12 and wing clamp 18 is inserted by friction fit into the longitudinal groove 28 formed in the central body 26 of the box clamp 14, as described and illustrated below in more detail. The pliable nature of the wing clamp 18 allows it to be forced through the narrowed opening portions of the longitudinal groove 28. Once positioned within the groove 28, the compressed portions of the wing clamp 18 expand to form a friction fit with the wall of the groove 28.

The holes 36 in the lateral wings 34 of the wing clamp 18 desirably are aligned with the downwardly extending posts 17 on the box clamp 14. It is understood that although the anchoring system 10 of the present invention is compatible with present winged retention systems which utilize two lateral, aligned suture holes in both the box clamp and the wing clamp, no particular limitation on the present invention should be intended or implied, since its principles are equally applicable to other retention devices of other configurations which include one or more mounting posts.

FIG. 2 further illustrates the retainer 20 of the anchoring system 10. The retainer 20 includes at least one and preferably a plurality of slotted holes 42 formed in the top surface thereof. These holes 42 are also in alignment with the holes 36 in the lateral wings 34 of the wing clamp 18 and the downwardly extending posts 17 of the box clamp 14. Each slotted hole 42 is formed by a central circular opening 42a, with at least one lateral slot or hole 42b extending to one side. In the illustrated embodiment, each slotted hole 42 includes a central opening 42a with lateral holes 42b extending to either side. As will be explained in more detail below, these slotted holes 42 receive the downwardly extending posts 17 of the box clamp 14 to provide releasable retention for the catheter 12.

FIG. 7 is a cross-sectional view of the retainer or anchor base 20 of the present invention and illustrates the slotted openings 42 formed on the upper surface thereof. Thus, within the retainer 20 and below each opening 42 there is found a hollow space 48 for receiving the tip 44 of the downwardly extending posts 17 of the box clamp 14. This space 48 also accommodates the lateral movement of the box clamp 14 in order to provide engagement between the neck 46 of each post 17 and one of the slots or holes 42b formed laterally with respect to the upper retainer hole 42a. In this manner, the tip 44 of each post 17 is captured within the hollow space 48 below each slot 42b. The post 17 cannot be pulled out of the hole 42 because the rear side of the tip 44 contacts the portion of the retainer 20 adjacent the slot 42b.

With reference to FIGS. 1 and 8, the retainer 20 desirably is secured to the anchor pad 22 by means of cyanoacrylate, or other bonding material. The flexible anchor pad 22 comprises a laminate structure formed by an upper paper or other woven or non-woven cloth layer, an inner cellulose foam layer, and a bottom adhesive layer. Alternatively, the flexible anchor pad 22 may comprise an adhesive bottom layer and an upper cellulose foam layer. An upper surface of the foam layer is roughened by corona treating the foam with a low electric charge, as known in the art. The roughened or porous upper surface of the anchor pad 22 improves cyanoacrylate (other types of adhesive or bonding materials) adhesion when attaching the retainer 20 to the anchor pad 22.

A removable paper or plastic backing (not shown) desirably covers the bottom adhesive surface before use. The backing preferably resists tearing and is divided into a plurality of pieces to ease attachment of the pad to the patient's skin. Desirably, the backing is split along a center line of the flexible anchor pad 22 in order to expose only half of the adhesive bottom surface at one time. The backing also advantageously extends beyond at least one edge of the anchor pad 22 to ease removal of the backing from the adhesive layer.

In the illustrated embodiment, the anchor pad 22 includes a pair of opposing concave sections which narrows the center of the anchor pad proximate to the retainer 22. As a result, the peripheral ends of the anchor pad 22 have more contact area to provide greater stability and adhesion to the patient's skin.

FIG. 8 illustrates the complete assembly of the anchoring system 10 of the present invention, including the self-adhesive foam pad 22, the retainer 20 secured to the upper foam surface of the anchor pad 22, and the catheter 12 which is retained in place by the engagement of the posts 17 of the box clamp 14 with the slotted holes 42 of the retainer 20. The wing clamp 18, which is sandwiched between the box clamp 14 and the catheter 12, as shown in FIG. 8, provides secure retention for the catheter 12 within the snap fit groove 28 of the box clamp 14.

In operation, the self-adhesive anchor pad 22 is applied to the skin 24 of the patient in the vicinity of the catheter insertion site. The anchor pad 22 should be mounted on the patient so that the retainer 20 is transverse to the catheter 12 and lies directly under it. The wing clamp 18 is then stretched and fit over the catheter 12, as in standard practice, and the downwardly extending posts 17 of the box clamp 14 are inserted through the holes 36 in the wings 34 of the wing clamp 18. The combination wing clamp/catheter is then snap fit into the longitudinal groove 28 of the box clamp 14 to form a secure engagement of those three elements. The posts 17 of the box clamp 14 are then aligned with the slotted openings 42 on the top surface of the retainer 20 such that the tip 44 of each post 17 passes through the corresponding large diameter hole 42a in the retainer 20. This engagement should be relatively easy so that downward force is not necessary, thereby avoiding pain or discomfort to the patient. Alternatively, the wing and box clamps 18, 14 may first engage the retainer 20, and subsequently the pad 22 may be affixed to the patient.

Once the tips 44 of the posts 17 have cleared the larger diameter opening 42a in the upper surface of the retainer 20 and have entered the hollow 48 there below (as shown in FIGS. 7 and 8), the box clamp 14 is slid laterally left or right so that the neck 46 of each post 17 slides into the lateral slots 42b of the retainer holes 42. The openings to each slots 42b desirably are sized so as to be slightly smaller than the diameter of the post necks 46, and they thereby provide a friction or snap fit engagement with the posts 17. This engagement serves to retain the box clamp combination securely in place within the retainer 20.

When removal becomes necessary, the box clamp 14 simply is slid horizontally in the opposite direction so that the tips 44 of the posts 17 are once again aligned with the larger diameter holes 42a, whereupon the box clamp combination can be easily removed vertically from the retainer 20 to allow the changing or cleaning of the catheter 12.

Thus, no painful or time-consuming sutures or other extensive removal procedures involving sharp instruments (e.g., scissors) are necessary with the anchoring system of the present invention. In addition, the anchor pad 22 absorbs any forces which are incurred in the installation or removal of the anchoring system and the catheter 12, thereby providing greater comfort for the patient.

Figure 9:
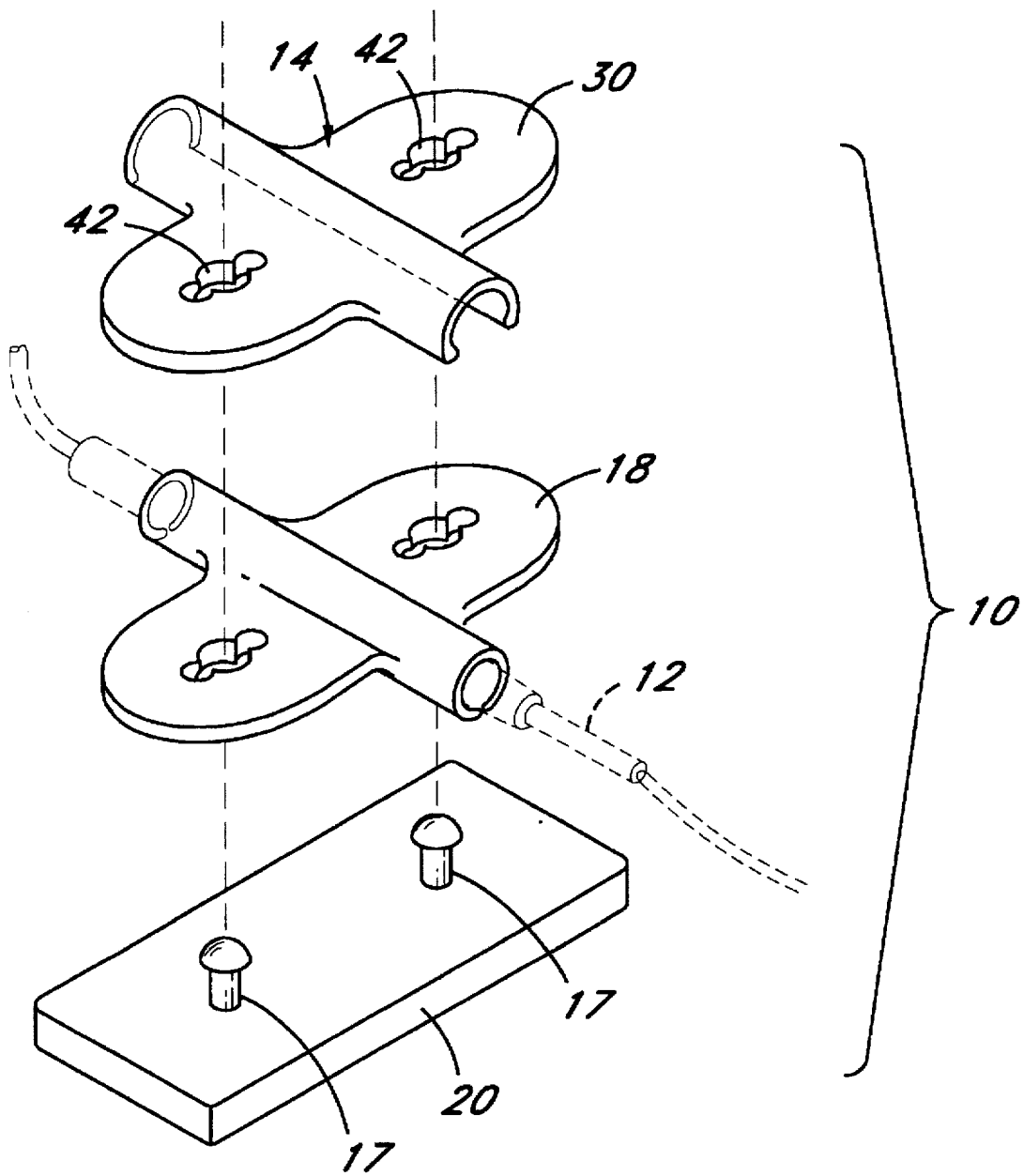
FIG. 9 is an exploded perspective view of an anchoring system in accordance with another preferred embodiment of the present invention.

Although this invention has been described in terms of a certain preferred embodiment, other embodiments apparent to those of ordinary skill in the art are also within the scope of this invention. For instance as seen in FIG. 9, it is appreciated that the retainer could include the post and the wings of the box clamp could define slotted holes which receive the corresponding posts. It also is understood that other types of known coupling mechanisms could be used as well to releasably secure the box clamp to the retainer. Accordingly, the scope of this invention is intended to be defined only by the claims which follow.

What is claimed is:

1. An anchoring system for securing a catheterization device to the body of a patient, said anchoring system comprising a clamp configured to releasably engage a portion of the catheterization device and a retainer connected to an adhesive layer for secure attachment to the body of the patient, said clamp and retainer including corresponding coupling structure which releasably engage to secure said clamp to said retainer, said coupling structure comprising at least one hole which receives a corresponding post, said post includes a flared end which has a size larger than at least a portion of said hole said hole having a first opening which is larger than said flared end of said post, and a second opening which is smaller than said flared end of said post.

2. The anchoring system of claim 1, wherein said retainer defines said hole and said post extends from said clamp.

3. The anchoring system of claim 1, wherein said clamp defines said hole and said post extends from said retainer.

4. The anchoring system of claim 1, wherein said post includes a shank which connected to said flared end, said shank being smaller in cross section than said second opening.

5. The anchoring system of claim 1, wherein said first and second openings are placed adjacent to each other.

6. The anchoring system of claim 5, wherein said post is configured to be freely inserted into said first opening and is able to be slid from said first opening to said second opening in which position said shank extends through said second opening and said flared end is captured behind said second opening.

7. The anchoring system of claim 6, wherein an intermediate opening section links said first and second openings together, said intermediate opening having a size slightly smaller than said post shank such that said second opening receives said post shank in a snap fit manner.

8. The anchoring system of claim 1 additionally comprising a flexible anchor pad, said adhesive layer formed on one side of said anchor pad and said retainer attached to an opposite side of said anchor pad.

9. The anchoring system of claim 8, wherein said anchor pad has a laminate structure formed by a cellulose foam layer interposed between said adhesive layer and a layer of woven fibers.

10. The anchoring system of claim 1 additionally comprising an pliable wing clamp configured to surround and engage a portion of the catheterization device, said wing clamp also being configured to engage said clamp.

11. The anchoring system of claim 10, wherein said clamp includes a groove which receives a portion of said wing clamp.

12. An anchoring system for securing a catheterization device to the body of a patient, said anchoring system comprising:

an anchor pad having an adhesive layer for secure attachment to the body of the patient;

a retainer attached to said pad;

a clamp configured to releasably engage a portion of the catheterization device; and a coupling to releasably interconnect said clamp and said retainer, said coupling comprising at least one post and at least one slotted hole, said slotted hole receiving said post in a first position and said post being movable from said first position to a second position within said hole, said coupling interconnecting said retainer and clamp with said post in said second position.

13. The anchoring system of claim 12, wherein said coupling includes a plurality of said posts and a plurality of said slotted holes.

14. The anchoring system of claim 13, wherein at least one of said posts extends from said clamp and at least one of said slotted holes is defined by said retainer.

15. The anchoring system of claim 13, wherein at least one of said posts extends from said retainer and at least one of said slotted holes in defined by said clamp.

16. The anchoring system of claim 13, wherein said clamp comprises a generally rigid element which defines a longitudinal groove and a generally pliable element which is configured to surround and engage a portion of the catheterization device, said pliable element being adapted to snap into said rigid element to secure the catheter within the clamp.

17. A method for attaching a catheterization device to a body of a patient, comprising the steps of:

providing a retainer coupled to an adhesive member;

providing a clamp configured to engage a portion of the catheterization device;

placing said adhesive member on the patient's body to secure the retainer thereon;

engaging said clamp with a portion of the catheterization device;

connecting said clamp to said retainer in a releasable manner; and releasing said clamp from said retainer in a manner which permits the clamp to be later reconnected to the retainer.

18. The method of claim 17, wherein coupling involves inserting a post with a flared end into a slotted hole at a first position and sliding said post within said slotted hole from said first position to a second position so as to capture said flared head behind a portion of said hole to prevent said post from pulling out of said slotted hole.

19. The method of claim 18, wherein said post is snapped into said second position from said first position so as to retain said post in said second position.

20. The method of claim 18, wherein releasing said clamp from said retainer involves sliding said post from said second position to said first position and thereafter withdrawing said post from said hole.

21. An anchoring system for securing a medical device to the body of a patient, said medical device including a cylindrical portion, said anchoring system comprising a clamp configured to releasably engage the cylindrical portion of the medical device and a retainer connected to an adhesive layer, said clamp and retainer comprising corresponding first and second members which releasably interconnect to couple together said clamp and retainer, said first member being movable relative to said second member and in a direction generally parallel to said adhesive layer from a first position in which said first and second members are disengaged to a second position in which said first and second members are engaged.

22. The anchoring system of claim 21, wherein said first member comprises a post with a flared end, and second member comprises a hole which receives said post, said hole having at least one portion which is larger than said flared end of said post, and another portion which is smaller than said flared end of said post.

23. The anchoring system of claim 22, wherein said retainer defines said hole and said post extends from said clamp.

24. The anchoring system of claim 22, wherein said clamp defines said hole and said post extends from said retainer.

25. The anchoring system of claim 22, wherein said clamp is adapted to engage a fluid tube of the medical device.

26. The anchoring system of claim 22, wherein said post is movable from said first position to said second position when inserted into said hole.

27. The anchoring system of claim 22, wherein said first member comprises a second post and said second member comprises a corresponding second hole which receives said second post.

28. An anchoring system for securing a medical device to the body of a patient, the medical device having an elongated portion which defines an axis, said anchoring system comprising a clamp configured to engage the elongated portion of the medical device, and a retainer coupled to an adhesive layer which adheres to the body of the patient, said clamp and retainer having corresponding coupling structures that engage to secure said clamp to said retainer, said coupling structure comprising an aperture having a major diameter lying generally perpendicular to the axis of the elongated portion engaged by the clamp, and a minor diameter lying generally parallel to the axis, said aperture being positioned to receive a corresponding post of said coupling structure, said post having a flared end of a size larger than at least a portion of said aperture.

29. The anchoring system of claim 28, wherein said post includes a shank connected to said flared end, said shank being smaller in cross section than said minor diameter.

30. The anchoring system of claim 29, wherein said shank of said post is configured to slide freely within said aperture along said major diameter with said flared end being captured on one side of said aperture.

31. The anchoring system of claim 29, wherein said aperture has a first opening which is larger than said flared end of said post, and a second opening which is smaller than said flared end of said post.

32. The anchoring system of claim 31, wherein said shank of said post has a smaller cross-sectional width than a diameter of said second opening.

33. The anchoring system of claim 31, wherein said first and second openings are placed adjacent to each other.

34. The anchoring system of claim 33, wherein said post is configured to be freely inserted into said first opening and to be slid from said first opening to said second opening in which position said shank extends through said second opening and said flared end is captured behind said second opening.

35. The anchoring system of claim 34, wherein an intermediate opening section links said first and second openings together, said intermediate opening having a size slightly smaller than the diameter of said post shank such that said second opening receives said post shank in a snap-fit manner.

36. The anchoring system of claim 28 additionally comprising a flexible anchor pad to which said adhesive layer is applied on one side of and said retainer is attached on an opposite side.

37. The anchoring system of claim 28 additionally comprising a pliable wing clamp configured to surround and engage a portion of the medical device, said wing clamp also being configured to engage said clamp.

38. The anchoring system of claim 37, wherein said clamp includes a channel which receives a portion of said wing clamp.

* * * * *